US012026837B2

(12) United States Patent
Berger et al.

(10) Patent No.: US 12,026,837 B2
(45) Date of Patent: Jul. 2, 2024

(54) ADAPTING AN AUGMENTED AND/OR VIRTUAL REALITY

(71) Applicant: Siemens Healthcare GmbH, Erlangen (DE)

(72) Inventors: Martin Berger, Erlangen (DE); Marcus Pfister, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 380 days.

(21) Appl. No.: 17/244,011

(22) Filed: Apr. 29, 2021

(65) Prior Publication Data

US 2021/0358220 A1    Nov. 18, 2021

(30) Foreign Application Priority Data

May 12, 2020    (DE) .................... 10 2020 205 976.4

(51) Int. Cl.
*G06T 19/00*    (2011.01)
*G06F 3/01*    (2006.01)
(Continued)

(52) U.S. Cl.
CPC ............ *G06T 19/006* (2013.01); *G06F 3/013* (2013.01); *G06F 3/167* (2013.01); *G06T 7/30* (2017.01)

(58) Field of Classification Search
CPC ..... G06T 19/006; G06T 7/30; G06T 2200/24; G06T 2210/41; G06T 2219/2016;
(Continued)

(56) References Cited

U.S. PATENT DOCUMENTS 6,083,163 A * 7/2000 Wegner .................. B25J 9/1679
606/130
7,991,105 B2    8/2011 Mielekamp et al.
(Continued)

FOREIGN PATENT DOCUMENTS

CN    104244833 A    12/2014
CN    105788390 A    7/2016
(Continued)

OTHER PUBLICATIONS

German Office Action for German Application No. 10 2020 205 976.4 dated Feb. 10, 2021.
(Continued)

*Primary Examiner* — Chong Wu
(74) *Attorney, Agent, or Firm* — Lempia Summerfield Katz LLC

(57) ABSTRACT

The disclosure relates to a display apparatus for displaying an augmented and/or virtual reality. The display apparatus has a sensor unit configured to capture a user input. The display apparatus is further configured to receive a medical planning dataset and receive a medical image dataset having at least one projection mapping. The display apparatus is further configured to generate and display the augmented and/or virtual reality based on the planning dataset and the at least one projection mapping. The display apparatus is further configured to adapt a virtual spatial positioning of the planning dataset relative to the at least one projection mapping in the augmented and/or virtual reality based on the user input. The disclosure further relates to a system, a method for registering a planning dataset with an image dataset, and a computer program product.

17 Claims, 8 Drawing Sheets

(51) Int. Cl.
  *G06F 3/16* (2006.01)
  *G06T 7/30* (2017.01)

(58) Field of Classification Search
  CPC ......... G06T 19/20; G06T 15/08; G06F 3/013;
    G06F 3/167; A61B 90/361; A61B 34/10;
    A61B 2017/00203; A61B 2017/00207;
    A61B 2017/00216; A61B 2090/365;
    A61B 2090/372; A61B 2090/376; A61B
    2090/502; A61B 90/37
  See application file for complete search history.

(56) References Cited

U.S. PATENT DOCUMENTS

| | | | | |
|---|---|---|---|---|
| 10,991,070 | B2* | 4/2021 | Saget | A61F 2/461 |
| 11,553,969 | B1* | 1/2023 | Lang | G06T 3/4007 |
| 2015/0071405 | A1 | 3/2015 | Jacobs | |
| 2018/0256256 | A1 | 9/2018 | May | |
| 2019/0015162 | A1 | 1/2019 | Abhari | |
| 2019/0054632 | A1 | 2/2019 | Grafenberg | |
| 2019/0080515 | A1 | 3/2019 | Geri | |
| 2020/0107904 | A1 | 4/2020 | Silva | |
| 2020/0221060 | A1* | 7/2020 | Casas | H04N 13/156 |
| 2021/0034148 | A1 | 2/2021 | Berger et al. | |

FOREIGN PATENT DOCUMENTS

| | | |
|---|---|---|
| CN | 107296650 A | 10/2017 |
| CN | 108882854 A | 11/2018 |
| CN | 109394252 A | 3/2019 |
| CN | 109464195 A | 3/2019 |
| CN | 110603002 A | 12/2019 |
| DE | 102019211536 A1 | 2/2021 |

OTHER PUBLICATIONS

Gong, Ren Hui, et al. "Interactive initialization of 2D/3D rigid registration." Medical physics 40.12 (2013): pp. 121911-1-121911-14.

Liao, Hongen, et al. "3-D augmented reality for MRI-guided surgery using integral videography autostereoscopic image overlay." IEEE transactions on biomedical engineering 57.6 (2010): 1476-1486.

Markelj, Primoz, et al. "A review of 3D/2D registration methods for image-guided interventions." Medical image analysis 16.3 (2012): 642-661.

Pratt, Philip, et al. "Through the HoloLens™ looking glass: augmented reality for extremity reconstruction surgery using 3D vascular models with perforating vessels." European radiology experimental 2.1 (2018): 1-7.

Stefan Luber et al. "What is Hololens" Bigdata Insider. https://www.bigdata-insider.de/was-ist-hololens-a-729042/Jun. 29, 2018. pp. 1-5.

* cited by examiner

ADAPTING AN AUGMENTED AND/OR VIRTUAL REALITY

The present patent document claims the benefit of German Patent Application No. 10 2020 205 976.4, filed May 12, 2020, which is hereby incorporated by reference in its entirety.

TECHNICAL FIELD

The present disclosure relates to a display apparatus for displaying an augmented and/or virtual reality, a system, a method for registering a planning dataset with an image dataset, and a computer program product.

BACKGROUND

For, in particular intraprocedural, support for a medical operating personnel, (e.g., a physician), in an examination and/or treatment of an examination object, preprocedural medical image data of the examination object may be used and displayed to the medical operating personnel. Therein, the preprocedural image data may have a preprocessed item of information, for example, for planning the procedure.

A particularly realistic representation of medical information, (for example, of the medical image data of the examination object), may be enabled by an imaging of an augmented and/or virtual reality (AR and/or VR). Herein, real objects, (for example, medical objects and/or the examination object), may be displayed overlaid with virtual data, in particular, medical image data and/or virtual objects, and represented in a display. For a realistic representation with a high degree of immersion, a precise registration within the virtual data and/or between the virtual data with the real objects is required. For this purpose, automated registration algorithms may be applied, based upon geometric and/or anatomical landmarks of the images. It is herein disadvantageous, however, that the known registration algorithms require a complex and simultaneously consistent annotation of the landmarks in the different image data. An inadequate annotation may thereby disadvantageously lead to poorer registration results.

SUMMARY AND DESCRIPTION

It is therefore an object of the disclosure to enable a particularly intuitive adaptation of an augmented and/or virtual reality.

The scope of the present disclosure is defined solely by the appended claims and is not affected to any degree by the statements within this summary. The present embodiments may obviate one or more of the drawbacks or limitations in the related art.

The disclosure relates, in a first aspect, to a display apparatus for displaying an augmented and/or virtual reality. The display apparatus has a sensor unit configured for capturing a user input. The display apparatus is further configured for receiving a medical image dataset having at least one projection mapping and for receiving a medical planning dataset. In addition, the display apparatus is configured for generating and displaying the augmented and/or virtual reality based on the planning dataset and the at least one projection mapping. Furthermore, the display apparatus is configured for adapting a virtual spatial positioning of the planning dataset relative to the at least one projection mapping in the augmented and/or virtual reality based on the user input.

The display apparatus may advantageously include a portable first display unit, (e.g., wearable by a user), which is configured for displaying the augmented and/or virtual reality (AR and/or VR). Therein, the first display unit may be configured to be at least partially see-through and/or transparent. Advantageously, the first display unit may be configured such that it is wearable by the user at least partially within a visual field of the user. For this purpose, the first display unit may advantageously be configured as glasses, (e.g., smart glasses), a helmet, (e.g., a head-mounted display), a screen, or a combination thereof.

Furthermore, the first display unit may be configured for displaying real objects, for example, physical, in particular medical, objects and/or the examination object overlaid with virtual data, in particular, scanned and/or simulated and/or processed medical image data and/or virtual objects in a display.

The sensor unit may include an optical sensor, an acoustic sensor, a haptic sensor, an electromagnetic sensor, or a combination thereof. Furthermore, the sensor unit may be arranged at least partially integrated into the first display unit. Alternatively or additionally, the sensor unit may be arranged at least partially on a body part of the user, for example, as a glove and/or a pointing facility, and/or on a medical device, in particular, a medical imaging device and/or in particular spatially fixed, in the space. Thereby, the sensor unit is advantageously configured for capturing the user input, in particular, based on an input device or system. The input device may include a pointing facility and/or an input unit and/or a body part of the user and/or an optical and/or acoustic signal. In particular, the user input may include a transformation instruction for adapting the virtual spatial positioning of the planning dataset relative to the at least one projection mapping in the augmented and/or virtual reality. For this purpose, the display apparatus may be configured for scaling the user input captured by the sensor unit.

Advantageously, the sensor unit may be configured for two-dimensional and/or three-dimensional capture of the user input, in particular, based on the input device or system. This may be enabled, in particular, during a capture of the user input by an optical sensor, a haptic sensor, an electromagnetic sensor, or a combination thereof. Thereby, the user input may have a trajectory, in particular, between a spatial start point and a spatial end point. The display apparatus may be configured for associating the spatial start point with the gripping point, in particular, on a corner and/or an edge and/or a contour and/or an image point of the planning dataset. Alternatively or additionally, the display apparatus may be configured for generating and displaying the augmented and/or virtual reality such that the planning dataset has at least one virtual, in particular activatable, operating element. Thereby, the display apparatus may also be configured for activating the at least one operating element through a user input and for associating it with the start point of the trajectory.

The display apparatus may advantageously have an interface configured for receiving the medical image dataset and/or the medical planning dataset. The interface may be configured for capturing and/or reading out a computer-readable data store and/or for receiving from a data storage unit, for example, a database. Furthermore, the display apparatus may have a provision unit which is configured for generating and/or adapting the augmented and/or virtual reality. Furthermore, the provision unit may be configured for processing the user input, in particular, a signal of the sensor unit, and/or the planning dataset and/or the image dataset. In addition, the medical image dataset and/or the medical planning dataset may be provided by a further provision unit of a medical imaging device. The medical planning dataset may be recorded and/or provided, with regard to the medical image dataset, by the same or a different medical imaging device. The medical imaging device may be configured as a medical X-ray device, (e.g., a medical C-arm X-ray device, a computed tomography (CT) system, a magnetic resonance (MRT) system, a positron emission tomography (PET) system, a sonography device, or a combination thereof).

Advantageously, the planning dataset and the image dataset may at least partially form a common examination region of an examination object. Therein, the examination object may be a human and/or animal patient and/or a phantom and/or workpiece. The examination region may be a spatial portion, in particular, a body region of the examination object. Therein, the planning dataset may map the examination region of the examination object, advantageously pre-procedurally. Furthermore, the image dataset may map the examination region, advantageously intra-procedurally. The image dataset may also have at least a projection mapping, (e.g., two-dimensional projection mapping), in particular, an X-ray projection mapping and/or a sonography projection mapping of the examination region. Advantageously, the image dataset, in particular, the at least one projection mapping may have an intraprocedural mapping of the examination region, wherein a medical object is arranged in the examination region. The medical object may be a surgical and/or diagnostic instrument, for example, a catheter and/or a guide wire and/or an endoscope. Advantageously, the at least one projection mapping may be recorded along a projection direction, in particular an angulation, by the medical imaging device. Furthermore, the image dataset may have a plurality of projection mappings of the examination region which are advantageously recorded along different projection directions by the medical imaging device. In addition, the image dataset, in particular, the projection mappings may be time resolved.

The planning dataset may advantageously have a two-dimensional and/or three-dimensional mapping of the examination region. In addition, the planning dataset may be time resolved.

The display apparatus may advantageously be configured for generating and displaying the augmented and/or virtual reality based on the planning dataset and the at least one projection mapping. In particular, the display apparatus may be configured for generating the augmented and/or virtual reality such that the planning dataset is displayed as spaced in relation to a graphical representation of the at least one projection mapping is displayed, in particular, two-dimensionally and/or three-dimensionally. In addition, the display apparatus may be configured for displaying at least one segmented portion of the planning dataset, (for example, a bone structure and/or a tissue region), in particular, three-dimensionally, for example, as a volumetric mesh model in the augmented and/or virtual reality. Furthermore, the display apparatus, in particular, the first display unit may be configured for displaying the planning dataset and/or the at least one projection mapping in the augmented and/or virtual reality at least partially transparent. The display apparatus may further be configured for generating and displaying the augmented and/or virtual reality locally fixed in relation to a real spatial environment of the user. For this purpose, the sensor unit configured for capturing a positioning change of the first display unit may be configured in relation to the real spatial environment of the user. For this purpose, the sensor unit may include a gyroscopic and/or optical and/or electromagnetic sensor. Furthermore, the display apparatus may be configured for generating the augmented and/or virtual reality such that both the planning dataset and also the at least one projection mapping are at least partially, in particular, simultaneously, visually perceivable by the user.

The sensor unit may advantageously be configured for capturing an initial spatial positioning of the user input, in particular, the input device or system at the start point. Therein, the initial spatial positioning may have an item of information regarding the spatial position, in particular, in relation to the sensor unit and/or in relation to a reference point and/or the spatial alignment of the captured input device or system at the start point. Furthermore, the captured initial spatial positioning of the user input may be registered with a virtual spatial position of the planning dataset, in particular, the gripping point. The virtual spatial positioning of the planning dataset, in particular, the gripping point, may have an item of information relating to the virtual spatial position and/or the alignment of the planning dataset in a coordinate system of the augmented and/or virtual reality.

Similarly thereto, the sensor unit may be configured for capturing a final spatial positioning of the user input, in particular, the input device or system, at the end point.

The display apparatus may be configured for adapting the virtual spatial positioning of the planning dataset, in particular, the gripping point, relative to the at least one projection mapping according to the user input. The virtual spatial positioning of the planning dataset may therein have an item of information relating to a virtual spatial position and/or alignment of the planning dataset, in particular, the gripping point, in the augmented and/or virtual reality. Furthermore, the virtual spatial positioning may be determined in relation to a coordinate system of the display apparatus, in particular, the first display unit. In addition, the virtual spatial positioning may have a relative positioning in relation to the at least one projection mapping. The display apparatus may be configured for repositioning the gripping point in the augmented and/or virtual reality from the start point to the end point. Furthermore, the display apparatus may be configured for adapting and displaying the augmented and/or virtual reality during and/or after the user input.

The proposed display apparatus enables a particularly intuitive adaptation of the augmented and/or virtual reality. Furthermore, through the adaptation of the virtual spatial positioning of the planning dataset relative to the at least one projection mapping in the augmented and/or virtual reality, a simple and, at the same time, precise registration may be enabled. In particular, a false alignment between the planning dataset and the at least one projection mapping may advantageously be lessened in the augmented and/or virtual reality. The user may therein advantageously adapt the virtual spatial positioning of the planning dataset by the user input, in particular simultaneously, along a plurality of spatial degrees of freedom in the augmented and/or virtual reality, in a simple and precise manner.

In a further advantageous embodiment of the proposed display apparatus, the display apparatus may also be configured for generating at least one planning projection mapping of the planning dataset. In addition, the display apparatus may be configured for generating and displaying the augmented and/or virtual reality additionally based on the at least one planning projection mapping. Furthermore, the display apparatus may be configured for adapting the at least one planning projection mapping on a change of the virtual spatial positioning of the planning dataset relative to the at least one projection mapping.

Advantageously, the image dataset may have metadata, wherein the metadata may have an item of information relating to a recording geometry and/or an operating parameter of the medical imaging device for recording the image dataset. Furthermore, the display apparatus may be configured, based on the metadata, to arrange a virtual source, for example, a virtual X-ray source and/or sonography source in the augmented and/or virtual reality in relation to the at least one projection mapping according to the respective recording geometry.

The at least one planning projection mapping may be a virtual projection mapping of the planning dataset along a virtual projection direction starting from the virtual source. The at least one planning projection mapping may have all the features and properties that have been described in relation to the at least one projection mapping and vice versa.

In addition, the display apparatus may be configured for generating and displaying the augmented and/or virtual reality having at least one virtual auxiliary element to the at least one projection mapping and/or the at least one planning projection mapping. The virtual auxiliary element may have a graphical representation of a projection cone and/or of a central ray of the virtual source along the respective, in particular, virtual projection direction. The sensor unit may therein be configured for capturing a further user input. Furthermore, the display apparatus may be configured for adapting the virtual projection direction to generate the at least one planning projection mapping based on the further user input. Therein, the capturing of the further user input may take place similarly to the capturing of the user input. Furthermore, the adaptation of the virtual projection direction for generating the at least one planning projection mapping may take place similarly to the adaptation of the virtual spatial positioning of the planning dataset in the augmented and/or virtual reality.

The display apparatus may be configured for generating the augmented and/or virtual reality such that the planning dataset is displayed as spaced in relation to a graphical representation of the at least one projection mapping and a graphical representation of the at least one planning projection mapping, in particular, two-dimensionally and/or three-dimensionally. Furthermore, the display apparatus may be configured for generating and displaying the at least one projection mapping and the at least one planning projection mapping in the augmented and/or virtual reality at least partially transparently and/or, in particular mutually, overlaid.

On a change of the virtual spatial positioning of the planning dataset relative to the at least one projection mapping, in particular, relative to the virtual source, the display apparatus may be configured for adapting the at least one planning projection mapping, in particular, to create it anew. The adaptation of the at least one planning projection mapping may include a virtual projection mapping of the planning dataset in the changed virtual spatial positioning along the virtual projection direction starting from the virtual source.

By the generation of the augmented and/or virtual reality, additionally based on the at least one planning projection mapping, a particularly intuitive and simultaneously precise repositioning of the planning dataset in relation to the, in particular virtual, projection direction may advantageously be enabled. Furthermore, an easily perceivable comparison between the at least one planning projection mapping and the at least one projection mapping may be enabled.

In a further advantageous embodiment of the proposed display apparatus, the display apparatus may also be configured for generating the at least one planning projection mapping along a projection direction of the at least one projection mapping.

Thereby, a projection direction of the at least one projection mapping may be specified, in each case, as a virtual projection direction for generating the at least one planning projection mapping. It may thereby be achieved that the mapping geometry for virtual projection mapping of the planning dataset along the at least one virtual projection direction starting from the virtual source advantageously corresponds to the recording geometry for recording the at least one projection mapping. Advantageously thereby, an intuitive repositioning of the planning dataset relative to the at least one projection mapping in the augmented and/or virtual reality is enabled such that the at least one planning projection mapping may be brought into conformity, in each case, with one of the at least one projection mapping. Thus, the examination region of the examination object mapped in the planning dataset may be virtually positioned in relation to the virtual source, the virtual projection direction and/or the at least one planning projection mapping such that a deviation between the mapping geometry for generating the at least one planning projection mapping and the recording geometry for recording the at least one projection mapping of the examination region is minimized.

In a further advantageous embodiment of the proposed display apparatus, the display apparatus may also be configured for generating a back projection of the at least one projection mapping. Furthermore, the display apparatus may be configured for generating and displaying the augmented and/or virtual reality additionally based on the at least one back projection. In addition, the display apparatus may be configured for adapting the at least one back projection on a change of the virtual spatial positioning of the planning dataset relative to the at least one projection mapping.

Advantageously, the image dataset may have metadata, wherein the metadata has an item of information relating to a recording geometry and/or an operating parameter of the medical imaging device for recording the image dataset. Furthermore, the display apparatus may be configured, based on the metadata, to arrange a virtual source, for example, a virtual X-ray source and/or a sonography source in the augmented and/or virtual reality in relation to the at least one projection mapping according to the respective recording geometry.

The at least one back projection may include a virtual, in particular, filtered back projection of the at least one projection mapping onto the planning dataset. Therein, the display apparatus may be configured for generating the at least one back projection along the projection direction of the respective projection mapping toward the virtual source.

The display apparatus may be configured for generating and displaying the at least one back projection and the planning dataset mapping in the augmented and/or virtual reality at least partially transparently and/or, in particular mutually, overlaid. In particular, the display apparatus may be configured for displaying the at least one back projection at least partially overlaid on a surface, for example, a segmented volumetric mesh model of at least a portion of the planning dataset, for example, a bone structure and/or a tissue region, in the augmented and/or virtual reality.

On a change of the virtual spatial positioning of the planning dataset relative to the at least one projection mapping, in particular, relative to the respective projection direction, the display apparatus may be configured for adapting the at least one back projection, in particular, to create it anew. The adaptation of the at least one back projection may include a virtual, in particular, filtered back projection of the at least one projection mapping onto the planning dataset in the amended virtual spatial positioning.

Through the generation of the augmented and/or virtual reality, additionally based on the at least one back projection, a particularly intuitive and simultaneously precise repositioning of the planning dataset in relation to the projection direction of the at least one projection mapping and/or back projection may advantageously be enabled. Furthermore, an easily perceivable comparison between the at least one back projection and the planning dataset in the augmented and/or virtual reality may be enabled. Thus, the examination region of the examination object mapped in the planning dataset may be virtually positioned in relation to the virtual source, the at least one projection direction and/or the at least one projection mapping such that an, in particular spatial, deviation between the at least one back projection and the planning dataset is minimized.

In a further advantageous embodiment of the proposed display apparatus, the display apparatus may also be configured for determining a transformation rule for adapting the virtual spatial positioning of the planning dataset relative to the at least one projection mapping based on the user input.

The display apparatus may be configured for determining the transformation rule based on the user input such that the planning dataset, in particular the gripping point, is repositioned from the start point to the end point when the transformation rule is used on the planning dataset in the augmented and/or virtual reality. Where the user input at the start point has an item of information regarding a spatial positioning of the input device or system, the display apparatus may be configured for associating the, in particular, initial, virtual spatial positioning of the planning dataset, in particular, the gripping point with the spatial positioning of the input device or system at the start point. Furthermore, the display apparatus may be configured for determining the transformation rule based on the captured change of the spatial positioning of the input device or system from the start point to the end point of the user input. Therein, the transformation rule may be configured for adapting the virtual spatial positioning of the planning dataset, in particular, the gripping point, in the augmented and/or virtual reality according to the captured change, in particular, along the trajectory. The transformation rule may include a rigid and/or non-rigid transformation of the planning dataset, in particular, in relation to the at least one projection mapping in the augmented and/or virtual reality. The display apparatus may be configured, in particular, to determine the transformation rule repeatedly during the capture of the user input.

By this, a particularly precise control of the repositioning of the planning dataset in the augmented and/or virtual reality by the user by the user input may be enabled.

In a further advantageous embodiment of the proposed display apparatus, the display apparatus may also be configured for specifying at least one spatial degree of freedom of the transformation rule based on a geometric property of the planning dataset and/or the image dataset.

The transformation rule may be formed for rigid and/or non-rigid transformation of the planning dataset in the augmented and/or virtual reality along at least one spatial degree of freedom, in particular, along a plurality of spatial degrees of freedom. Therein, the at least one spatial degree of freedom may be a movement degree of freedom of a virtual rotation movement and/or of a virtual translation movement and/or of a scaling of the planning dataset. Advantageously, the display apparatus may be configured for specifying the at least one spatial degree of freedom of the transformation rule based on a geometric property of the planning dataset and/or of the image dataset. The geometric property may therein have an item of information regarding the recording geometry of the planning dataset and/or of the image dataset. Furthermore, the geometric property may include an item of information regarding the positioning of the examination region of the examination object regarding the medical imaging device, in particular, in relation to a source and/or a detector, the recording of the planning dataset and/or the image data. Furthermore, the geometric information may include an item of information regarding the spatial configuration of the planning dataset and/or of the image data, for example, an item of extent information and/or of alignment information and/or of positioning information and/or of depth information. Advantageously, through the specification of the at least one spatial degree of freedom of the transformation rule based on the geometric property of the planning dataset and/or of the image dataset, an, in particular undesirable and/or non-physical, transformation of the planning dataset in the augmented and/or virtual reality may be prevented. For example, a virtual rotation movement of the planning dataset may be permitted, in particular arbitrarily, whereas a virtual translation movement of the planning dataset is permitted only in a predefined spatial region and/or along a predefined spatial direction within the augmented and/or virtual reality. In particular, a virtual movement of the planning dataset relative to at least one projection mapping by the at least one degree of freedom of the transformation rule may be delimited such that a movement into one another of the planning dataset and the at least one projection mapping (out-of-plane) is prevented.

In a further advantageous embodiment of the proposed display apparatus, the sensor unit may include an optical sensor, a haptic sensor, an electromagnetic sensor, an acoustic sensor, an eye tracker, or a combination thereof. Therein, the sensor unit may be configured for capturing the user input, a positioning and/or a movement of at least one body part of the user and/or a speech input by the user and/or a gaze direction of the user.

Therein, the optical sensor may include a camera, (e.g., a mono camera, a stereo camera, a depth camera, or a combination thereof). Advantageously, the optical sensor may be configured for capturing a spatial positioning and/or movement of the at least one body part of the user, in particular, in relation to the display apparatus. Furthermore, the sensor unit may be configured for capturing an, in particular, spatially and/or temporally resolved input gesture of the user, in particular, the input device or system, as user input. In addition, the haptic sensor may include a control element which is operable by a body part of the user, (e.g., a joystick, a pointing facility, a haptic controller, a haptic glove, or a combination thereof). The electromagnetic sensor may be configured to capture a movement of a body part and/or an input the user based on a change in an electromagnetic field around the display apparatus. The acoustic sensor may include at least one microphone configured for capturing a speech input of the user, for example, a speech command and/or an acoustic signal. Furthermore, the sensor unit may have an eye tracker configured for capturing a gaze direction of the user in relation to the display of the augmented and/or virtual reality. In particular, the sensor unit may be arranged integrated at least partially into the display apparatus, in particular, the first display unit.

The sensor unit may have a plurality of different sensors for capturing the user input. For example, at least one of the sensors may be configured for capturing the user input for specifying and/or selecting the gripping point. Furthermore, at least one further sensor is configured for capturing the user input for the adaptation of the virtual spatial positioning of the planning dataset. By this, a particularly intuitive and flexible operation of the display apparatus by a user is enabled. In particular, in a surgical environment, a high flexibility in the manner of capturing the user input by the sensor unit may be advantageous.

In a further advantageous embodiment of the proposed display apparatus, the planning dataset and/or the image dataset may have a predetermined item of image information. Therein, the display apparatus may be configured for generating and displaying the augmented and/or virtual reality additionally based on the predetermined image information.

The display apparatus may be configured for receiving and/or generating the predetermined image information, in particular, based on the planning dataset and/or the image dataset. The predetermined image information may include a preprocessed image information item, for example, an image gradient and/or an edge image and/or a probability image having an item of probability information with regard to the presence of a particular structure. Alternatively or additionally, the predetermined image information may include a two-dimensional segmentation of, in particular anatomical, landmarks and/or structures, (e.g., a vessel, a bone structure, an organ, a tissue region, or combination thereof), and/or a medical object, (e.g., a catheter, a guide wire, an endoscope, or combination thereof).

Where the planning dataset has a predetermined item of image information, the display apparatus may be configured for generating and displaying the augmented and/or virtual reality additionally based on the predetermined image information of the planning dataset such that this predetermined image information is perceivable by the user. For this purpose, the display apparatus may be configured for displaying the predetermined image information of the planning dataset, for example, graphically on a two-dimensional and/or three-dimensional surface of the planning dataset in the augmented and/or virtual reality, for example, as an overlay. Alternatively or additionally, the display apparatus may be configured for imaging the predetermined image information of the planning dataset similarly to the planning projection mapping. In particular, the display apparatus may be configured for displaying the predetermined image information of the planning dataset as part of the planning projection mapping.

Where the image dataset has a predetermined item of image information, the display apparatus may be configured for generating and displaying the augmented and/or virtual reality additionally based on the predetermined image information of the image dataset such that this predetermined image information of the image dataset is perceivable by the user. For this purpose, the display apparatus may be configured for displaying the predetermined image information of the image dataset graphically in the augmented and/or virtual reality, for example, as an overlay with the at least one projection mapping. Alternatively or additionally, the display apparatus may be configured for imaging the predetermined image information of the image dataset similarly to the back projection. In particular, the display apparatus may be configured for displaying the predetermined image information of the image dataset as part of the back projection on the planning dataset in the augmented and/or virtual reality.

The incorporation of the predetermined image information of the planning dataset and/or the image dataset into the generation and/or representation of the augmented and/or virtual reality may provide a visual aid to the user for adapting the virtual spatial positioning of the planning dataset. By this, a rapid and simultaneously precise capture of deviations in the augmented and/or virtual reality by the user may be enabled, for example, between the planning dataset and the back projection and/or between the at least one planning projection mapping and the at least one projection mapping.

In a further advantageous embodiment of the proposed display apparatus, the display apparatus may further be configured for selecting the predetermined image information based on the user input, in particular, from a number of received predetermined items of image information, for example, through the display of a preview and/or a menu in the augmented and/or virtual reality. Alternatively or additionally, the display apparatus may be configured for generating the predetermined image information based on the user input. For this, the user may specify an image point, a mapping of an anatomical structure, a geometric structure, a medical object, or a combination thereof in the augmented and/or virtual reality, (e.g., in the planning dataset and/or the at least one projection mapping), by the user input.

The proposed embodiment enables a particularly user-friendly display of assistance for adapting the virtual spatial positioning of the planning dataset in the augmented and/or virtual reality.

In a further advantageous embodiment of the proposed display apparatus, the display apparatus may have a first and a second display unit. Herein, the first display unit may be configured for displaying the augmented and/or virtual reality. Furthermore, the second display unit may be configured for displaying the at least one projection mapping and/or the at least one planning projection mapping. In addition, the sensor unit may be configured for capturing a spatial relative positioning of the first and the second display unit relative to one another. Therein, the display apparatus may be configured for adapting the augmented and/or virtual reality based on the captured relative positioning.

The spatial relative positioning of the first and the second display unit to one another may include an item of information regarding the spatial position and/or alignment of the first and the second display unit relative to one another.

The second display unit may include a monitor and/or a display. Therein, the sensor unit may be configured for at least partially capturing the second display unit, in particular, a spatial relative positioning of the second display unit in relation to the first display unit. Where the sensor unit is arranged at least partially integrated into the first display unit, a capture of the second display unit may suffice for determining the spatial relative positioning. Alternatively, the sensor unit may be configured for capturing the first and the second display unit, in particular, relative to one another and/or absolutely in relation to a spatial reference point. The first and/or the second display unit may have a defined form and/or a marker structure. Alternatively or additionally, the sensor unit may be configured for capturing the representation of at least one projection mapping and/or the at least one planning projection mapping on the second display unit. Furthermore, the first and/or the second display unit may be configured for providing a signal including an item of information for spatial positioning on the sensor unit. For this purpose, the first and/or second display unit may have a positioning sensor, (e.g., a gyroscopic sensor, an optical sensor, an electromagnetic sensor, or a combination thereof).

Advantageously, the display apparatus may be configured for adapting the augmented and/or virtual reality based on the captured relative positioning such that the representation of the at least one projection mapping and/or the at least one planning projection mapping is at least partially embedded and/or integrated on the second display unit into the augmented and/or virtual reality. The display apparatus, in particular, the first display unit may be configured for displaying the augmented and/or virtual reality via the representation on the second display unit at least partially overlaid.

By this, a particularly simple integration of the augmented and/or virtual reality into an existing working environment of the user having the second display unit may be enabled. Therein, the proposed display apparatus may display perceivably to the user additional information in the at least partially overlaid representation of the first and second display unit.

The disclosure relates, in a second aspect, to a system including a display apparatus according to one of the preceding claims and a medical imaging device. The medical imaging device is therein configured for recording and/or for providing and/or for receiving the planning dataset and/or the image dataset.

The advantages of the proposed system substantially correspond to the advantages of the proposed display apparatus for providing an augmented and/or virtual reality. Features, advantages, or alternative embodiments mentioned herein may also be transferred to the other claimed subject matter and vice versa.

The medical imaging device may be configured as a medical X-ray device, (e.g., a medical C-arm X-ray device, a computed tomography (CT) system, a magnetic resonance (MRT) system, a positron emission tomography (PET) system, a sonography device, or a combination thereof). Therein, the medical imaging device may further be configured for one or more of recording, receiving, or providing the planning dataset and/or the image dataset.

The medical imaging device may have an interface configured for providing and/or receiving the medical image dataset and/or the medical planning dataset, in particular, to the display apparatus. The interface may be configured for capturing and/or reading out a computer-readable data store and/or for receiving from a data storage unit, for example, a database.

The disclosure relates, in a third aspect, to a method for registering a planning dataset with an image dataset. Therein, in act a), a planning dataset of an examination object is received. Furthermore, in act b), an image dataset having at least one projection mapping of the examination object is received. In act c), an augmented and/or virtual reality is generated based on the planning dataset and the at least one projection mapping. In act d), a graphical display of the augmented and/or virtual reality is displayed by a display apparatus having a sensor unit. In act e), a user input is captured by the sensor unit. Furthermore, in act f), a virtual spatial positioning of the planning dataset relative to the at least one projection mapping is adapted in the augmented and/or virtual reality based on the user input.

The advantages of the proposed method correspond substantially to the advantages of the proposed display apparatus for displaying an augmented and/or virtual reality and/or the proposed system. Features, advantages, or alternative embodiments mentioned herein may also be transferred to the other claimed subject matter and vice versa.

The acts a) to f) of the proposed method described above may advantageously be carried out sequentially and/or at least partially simultaneously. Advantageously, the acts a) to f) of the proposed method may be carried out by a proposed display apparatus. In particular, the display of the graphical representation of the augmented and/or virtual reality may take place in act d) by the proposed display apparatus, in particular, the first display unit.

Advantageously, through the adaptation of the virtual spatial positioning of the planning dataset relative to the at least one projection mapping in the augmented and/or virtual reality in act f), a registration between the planning dataset and the image dataset, in particular, the at least one projection mapping may be improved. Advantageously, the planning dataset in the augmented and/or virtual reality may be positioned based on the user input such that a virtual spatial positioning of the examination region mapped therein of the at least one projection mapping has a high level of conformity with a spatial positioning of the examination region at the time point of the recording of the at least one projection mapping in relation to the at least one projection mapping. Hereby, a particularly exactly fitting representation of the planning dataset and the at least one projection mapping in the augmented and/or virtual reality may advantageously be enabled.

In a further advantageous embodiment of the proposed method, the acts d) to f) may be carried out repeatedly until the occurrence of a termination condition. The termination condition may include a maximum number of repetitions. Alternatively or additionally, the termination condition may be triggered by a predefined user input, for example, a predefined gesture by the user.

Hereby, an, in particular iterative, adaptation of the virtual relative positioning of the planning dataset relative to the at least one projection mapping in the augmented and/or virtual reality may be enabled.

In a further advantageous embodiment of the proposed method, act c) may further include an application of a transformation rule for registering the planning dataset with the image dataset.

Therein, the transformation rule may be determined based on the user input such that the planning dataset, in particular the gripping point, is repositioned from the start point to the end point when the transformation rule is applied to the planning dataset in the augmented and/or virtual reality. Where the user input at the start point has an item of information regarding a spatial positioning of the input device or system, the (e.g., initial), virtual spatial positioning of the planning dataset, (e.g., the gripping point), may be associated with the spatial positioning of the input device or system at the start point. Furthermore, the transformation rule may be determined based on the captured change of the spatial positioning of the input device or system from the start point to the end point of the user input. Therein, the transformation rule may be configured for adapting the virtual spatial positioning of the planning dataset, (e.g., the gripping point), in the augmented and/or virtual reality according to the captured change, in particular, along the trajectory. The transformation rule may herein include a rigid and/or non-rigid transformation of the planning dataset, in particular, in relation to the at least one projection mapping in the augmented and/or virtual reality. The transformation rule may be determined repeatedly during the capturing of the user input in act e).

By this, a particularly precise control of the repositioning of the planning dataset in the augmented and/or virtual reality by the user may be enabled by the user input.

In a further advantageous embodiment of the proposed method, act c) may further include a generation of at least one planning projection mapping of the planning dataset along a projection direction of the at least one projection mapping. Therein, the augmented and/or virtual reality may additionally be generated based on the at least one planning projection mapping. Furthermore, act f) may include an adaptation of the at least one planning projection mapping on a change of the virtual spatial positioning of the planning dataset relative to the at least one projection mapping.

Similarly to one of the embodiments described above of the proposed method, the image dataset may have metadata, wherein, based on the metadata, a virtual source may be arranged in the augmented and/or virtual reality in relation to the at least one projection mapping according to the respective recording geometry. The at least one planning projection mapping may be a virtual projection mapping of the planning dataset along a virtual projection direction starting from the virtual source. The at least one planning projection mapping may have all the features and properties that have been described in relation to the at least one projection mapping and vice versa.

The augmented and/or virtual reality may advantageously be generated and displayed in acts c) and d) such that it has at least one virtual auxiliary element to the at least one projection mapping and/or the at least one planning projection mapping. The virtual auxiliary element may have a graphical representation of a projection cone and/or of a central ray of the virtual source along the respective, in particular, virtual and/or real projection direction. The sensor unit may therein be configured for capturing a further user input. Furthermore, the virtual projection direction may be configured to generate the at least one planning projection mapping based on the further user input. Therein, the capturing of the further user input may take place similarly to the capturing of the user input. Furthermore, the adaptation of the virtual projection direction for generating the at least one planning projection mapping may take place similarly to the adaptation of the virtual spatial positioning of the planning dataset in the augmented and/or virtual reality.

The augmented and/or virtual reality may advantageously be generated such that the planning dataset is displayed as spaced in relation to a graphical representation of the at least one projection mapping and a graphical representation of the at least one planning projection mapping, in particular, two-dimensionally and/or three-dimensionally. Furthermore, the at least one projection mapping and the at least one planning projection mapping in the augmented and/or virtual reality are displayed at least partially transparent and/or, in particular mutually, overlaid.

On a change of the virtual spatial positioning of the planning dataset relative to the at least one projection mapping, in particular, relative to the virtual source, the at least one planning projection mapping may be adapted, in particular, created anew. The adaptation of the at least one planning projection mapping may include a virtual projection mapping of the planning dataset in the changed virtual spatial positioning along the virtual projection direction starting from the virtual source.

By the generation of the augmented and/or virtual reality, additionally based on the at least one planning projection mapping, a particularly intuitive and simultaneously precise repositioning of the planning dataset in relation to the, in particular virtual, projection direction may advantageously be enabled. Furthermore, an easily perceivable comparison between the at least one planning projection mapping and the at least one projection mapping may be enabled.

In a further advantageous embodiment of the proposed method, the termination condition may include a comparison between a similarity measure (or degree of conformity) and a specified threshold value. The similarity measure may evaluate a conformity between the at least one planning projection mapping and the at least one projection mapping.

The threshold value may be input and/or specified, for example, by a user.

The similarity measure may advantageously include an item of information regarding an, in particular, image pointwise conformity between the at least one planning projection mapping and at least one portion of the planning dataset, in particular, along mutually corresponding real and virtual projection directions. The similarity measure may be determined based on a conformity metric. Furthermore, the similarity measure may be determined based on a comparison of image values and/or geometric features and/or anatomical features between the at least one planning projection mapping and the at least one projection mapping. Therein, a high level of conformity between the at least one planning projection mapping and the at least one projection mapping may be achieved if the planning dataset is virtually repositioned in relation to the at least one projection mapping and/or in relation to the respective projection direction substantially similarly to the mapping geometry of the examination region, in particular, at the time point of the recording of the at least one projection mapping. Therein, the similarity measure may further be determined such that the similarity measure has a different weighting and/or scaling along the degrees of freedom of the transformation rule. By this, a particularly precise registration of the planning dataset with the image dataset, in particular, with the at least one projection mapping may be enabled.

In a further advantageous embodiment of the proposed method, act c) may further include a generation of a back projection of the at least one projection mapping. Therein, the augmented and/or virtual reality may additionally be generated based on the at least one back projection. In addition, act f) may include an adaptation of the at least one back projection on a change of the virtual spatial positioning of the planning dataset relative to the at least one projection mapping.

Advantageously, the image dataset may have metadata, wherein the metadata has an item of information relating to a recording geometry and/or an operating parameter of the medical imaging device for recording the image dataset. Furthermore, based on the metadata, a virtual source, for example, a virtual X-ray source and/or a sonography source may be arranged in the augmented and/or virtual reality in relation to the at least one projection mapping according to the respective recording geometry.

The at least one back projection may advantageously include a virtual, in particular, filtered back projection of the at least one projection mapping onto the planning dataset. Therein, the at least one back projection may be generated along the projection direction of the respective projection mapping toward the virtual source. The augmented and/or virtual reality may advantageously be generated such that therein the at least one back projection and the planning dataset are displayed at least partially transparent and/or, in particular mutually, overlaid. The at least one back projection may be displayed at least partially overlaid onto a surface, for example, a segmented volumetric mesh model of at least a portion of the planning dataset, for example, a bone structure and/or a tissue region in the augmented and/or virtual reality.

On a change of the virtual spatial positioning of the planning dataset relative to the at least one projection mapping, in particular, relative to the respective projection direction, the at least one back projection may be adapted, in particular, created anew. The adaptation of the at least one back projection may advantageously include a virtual, in particular, filtered back projection of the at least one projection mapping onto the planning dataset in the changed virtual spatial positioning.

Through the generation of the augmented and/or virtual reality, additionally based on the at least one back projection, a particularly intuitive and simultaneously precise repositioning of the planning dataset in relation to the projection direction of the at least one projection mapping and/or back projection may advantageously be enabled. Furthermore, an easily perceivable comparison between the at least one back projection and the planning dataset in the augmented and/or virtual reality may be enabled. Thus, the examination region of the examination object mapped in the planning dataset may be virtually positioned in relation to the virtual source, the at least one projection direction and/or the at least one projection mapping such that an, in particular spatial, deviation between the at least one back projection and the planning dataset is minimized.

In a further advantageous embodiment of the proposed method, the termination condition may include a comparison between a further similarity measure (or further degree of conformity) and a specified threshold value. Therein, the further similarity measure may evaluate a conformity between the at least one back projection and the planning dataset.

The further threshold value may be input and/or specified, for example, by a user.

The further similarity measure may advantageously include an item of information regarding a conformity between the at least one back projection and at least one portion of the planning dataset, in particular, the portion of the planning dataset on which the back projection is mapped. The further similarity measure may be determined, in particular, based on a conformity metric, in particular image point-wise. Furthermore, the further similarity measure may be determined, for example, based on a comparison of image values and/or geometric features and/or anatomical features between the planning dataset and the at least one back projection. Therein, a high level of conformity between the planning dataset and the at least one back projection may be achieved if the planning dataset is virtually repositioned in relation to the at least one back projection, in particular, in relation to the at least one projection mapping and/or in relation to the respective projection direction substantially similarly to the mapping geometry of the examination region, in particular, at the time point of the recording of the at least one projection mapping. Therein, the further similarity measure may further be determined such that the further similarity measure along the degrees of freedom of the transformation rule has an, in particular, different weighting and/or scaling. By this, a particularly precise registration of the planning dataset with the image dataset, in particular, with the at least one projection mapping may be enabled.

In a fourth aspect, the disclosure relates to a computer program product with a computer program which is loadable directly into a memory store of a provision unit, having program portions in order to carry out all the acts of the proposed method for registering a planning dataset with an image dataset when the program portions are executed by the provision unit. The computer program product may include an item of software with a source code which is compiled and linked, or which is only interpreted, or an executable software code which, for execution, is only loaded into the provision unit. By the computer program product, the method for registering a planning dataset with an image dataset may be carried out rapidly by a provision unit, exactly reproducibly and robustly. The computer program product is configured such that it may carry out the method acts by the provision unit.

The computer program product is stored, for example, on a computer-readable storage medium or is deposited on a network or server from where it may be loaded into the processor of a provision unit, which may be directly connected to the provision unit, or which may be configured as part of the provision unit. Furthermore, control information of the computer program product may be stored on an electronically readable data carrier. The items of control information of the electronically readable data carrier may be configured such that they carry out a method when the data carrier is used in a provision unit. Examples of electronically readable data carriers are a DVD, a magnetic tape, or a USB stick, on which electronically readable control information, in particular software, is stored. If these items of control information are read from the data carrier and stored in a provision unit, all the embodiments of the above-described methods may be carried out.

The disclosure may also relate to a computer-readable storage medium and/or an electronically readable data carrier on which program portions that may be read in and executed by a provision unit are stored in order to carry out all the acts of the method for registering a planning dataset with an image dataset when the program portions are executed by the provision unit.

A realization largely through software has the advantage that conventionally used provision units may also easily be upgraded with a software update in order to operate in the manner according to the disclosure. Such a computer program product may include, where relevant, in addition to the computer program, additional constituents, such as, for example, documentation and/or additional components as well as hardware components, for example, hardware keys (dongles, etc.) in order to use the software.

BRIEF DESCRIPTION OF THE DRAWINGS

Exemplary embodiments of the disclosure are illustrated in the drawings and are described in greater detail below. In the different figures, the same reference signs are used for the same features. In the drawings.

DETAILED DESCRIPTION

Figure 1:
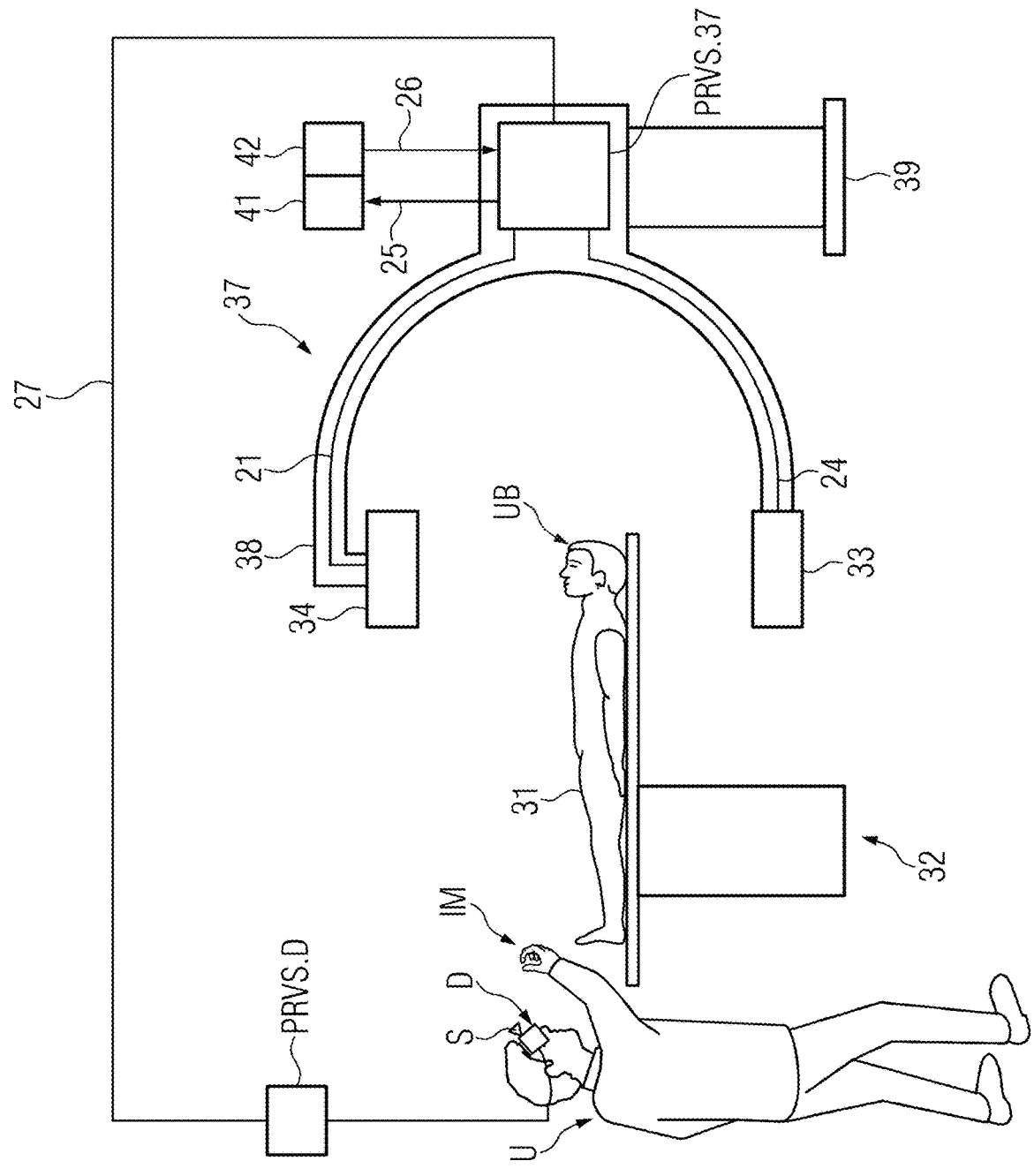
FIG. 1 depicts a schematic representation of an example of a system having a display apparatus and a medical C-arm X-ray device.

FIG. 1 depicts a proposed system schematically. The system may therein include a proposed display apparatus D and a medical imaging device. Furthermore, the medical imaging device may be configured as a medical C-arm X-ray device 37. Therein, the display apparatus D may have a provision unit PRVS.D which is configured for generating and/or adapting an augmented and/or virtual reality. Furthermore, the medical C-arm X-ray device 37 may include a further provision unit PRVS.37. Therein, the display apparatus D, in particular, the provision unit PRVS.D may be configured for carrying out a proposed method for registering a planning dataset with an image dataset.

Furthermore, the medical C-arm X-ray device 37 may have a detector unit 34 and an X-ray source 33 which may be mounted movable about one or more axes on an arm 38 of the C-arm X-ray device 37. Furthermore, the medical C-arm X-ray device 37 may include a movement apparatus 39, which enables a movement of the C-arm X-ray device 37 in the space. For recording the medical image dataset having at least one projection mapping and/or the planning dataset from an examination region UB of an examination object 31 arranged on a patient positioning apparatus 32. The further provision unit PRVS.37 may transmit a signal 24 to the X-ray source 33. Thereupon, the X-ray source 33 may emit an X-ray beam, in particular, a conical beam and/or a fan beam and/or a parallel beam. When the X-ray beam impinges upon a surface of the detector unit 34 following an interaction with an examination region of the examination object 31 to be mapped, the detector unit 34 may transmit a signal 21 to the further provision unit PRVS.37. The further provision unit PRVS.37 may receive the image dataset, for example, based on the signal 21 and/or the planning dataset. Furthermore, the further provision unit PRVS.37 may provide the image dataset and/or the planning dataset for generating the augmented and/or virtual reality to the display apparatus D, in particular the provision unit PRVS.D. For this purpose, the further provision unit PRVS.37 may transmit a corresponding signal 27, in particular, wirelessly to the display apparatus D, in particular, the provision unit PRVS.D.

Advantageously, the display apparatus D may have a sensor unit S which is configured for capturing a user input, in particular an input device or system IM. The input device or system IM may include a pointing facility, an input unit, a body part of the user, an optical signal, an acoustic signal, or a combination thereof. Furthermore, the display apparatus D may be configured for receiving the medical image dataset having at least one projection mapping and the medical planning dataset, in particular, by the signal 27. Therein, the provision unit PRVS.D may be configured for processing the user input, in particular, a signal from the sensor unit S and/or the planning dataset and/or the image dataset. Furthermore, the display apparatus D may be configured for generating and displaying the augmented and/or virtual reality. Furthermore, the display apparatus D may be configured for adapting a virtual spatial positioning of the planning dataset relative to the at least one projection mapping in the augmented and/or virtual reality based on the user input.

The display apparatus D may advantageously include a portable first display unit which is, in particular, wearable by a user, and is configured for displaying the augmented and/or virtual reality (AR and/or VR). Therein, the first display unit may be configured at least partially see-through and/or transparent. Advantageously, the first display unit may be configured such that it is wearable by the user U at least partially within a visual field of the user U. For this purpose, the first display unit may advantageously be configured as glasses, (e.g., smart glasses), a helmet, (e.g., a head-mounted display), a screen, or a combination thereof.

Furthermore, the first display unit may be configured for displaying real objects, for example, physical, in particular medical, objects and/or the examination object 31 overlaid with virtual data, in particular, scanned and/or simulated and/or processed medical image data and/or virtual objects and to represent them in a display.

The sensor unit S may further include an optical sensor, a haptic sensor, an electromagnetic sensor, an acoustic sensor, an eye tracker, or a combination thereof. Therein, the sensor unit S may be configured, for capturing the user input, to capture a positioning and/or a movement of at least one body part of the user U and/or a speech input by the user U and/or a gaze direction of the user U.

In addition, the medical C-arm X-ray device 37 may include an input unit 42, (e.g., a keyboard), and/or a second display unit 41, (e.g., a monitor and/or a display). The input unit 42 may be integrated into the second display unit 41, for example, in the case of a capacitive input display. Therein, by an input by the user U to the input unit 42, a control of the medical C-arm X-ray device 37 may be enabled. For this purpose, the input unit 42 may transmit, for example, a signal 26 to the further provision unit PRVS.37.

Furthermore, the second display unit 41 may be configured for displaying information and/or graphical representations of information of the medical C-arm X-ray device 37 and/or the provision unit PRVS.D and/or the further provision unit PRVS.37 and/or further components. In addition, the second display unit 41 may be configured for displaying the at least one projection mapping. For this purpose, the provision unit PRVS.37 may transmit, for example, a signal 25 to the second display unit 41.

In addition, the sensor unit S may be configured for capturing a spatial relative positioning of the first and the second display unit 41. Herein, the display apparatus D may be configured for adapting the augmented and/or virtual reality based on the captured relative positioning.

Figure 2:
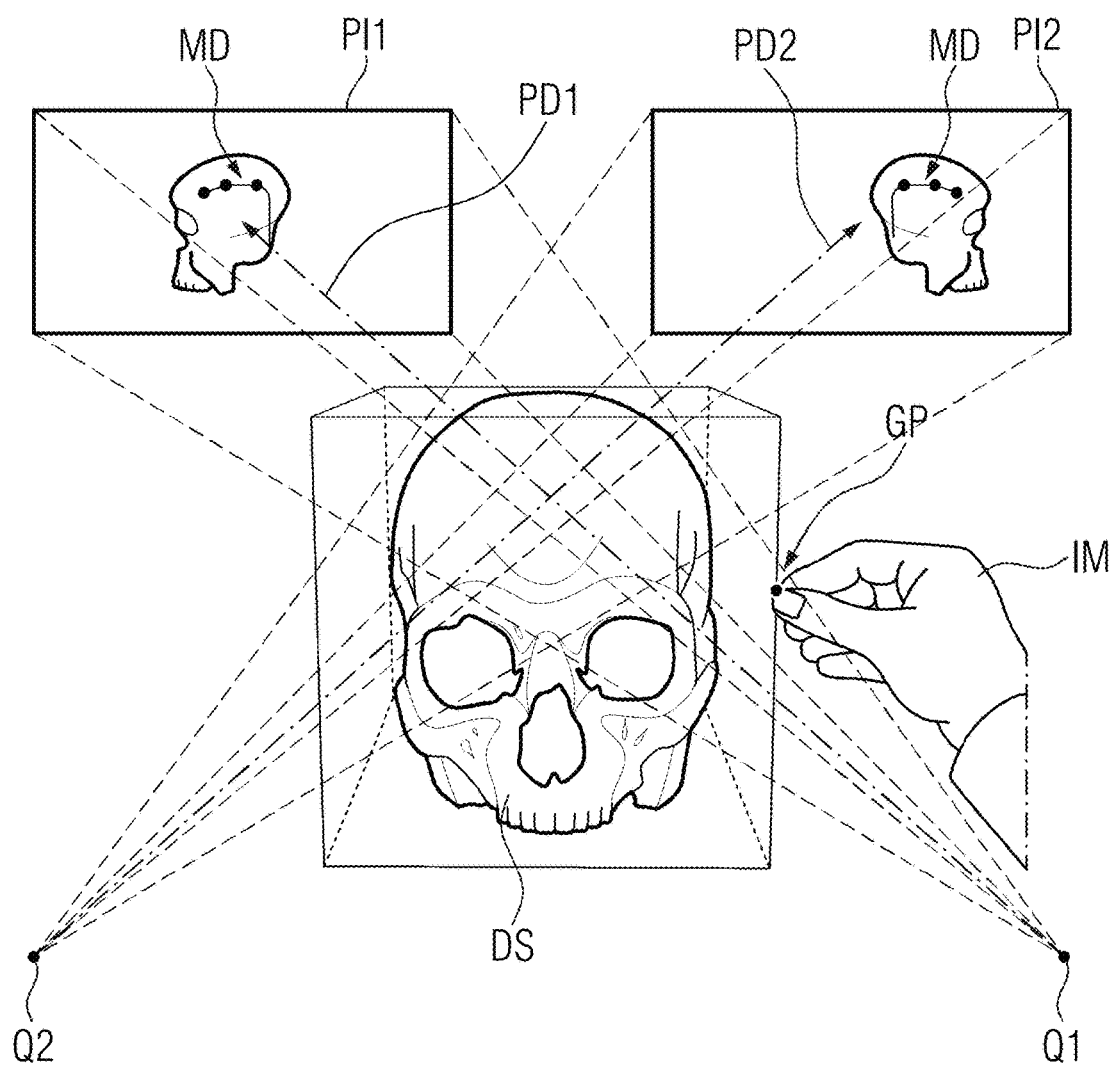
FIGS. 2 to 5 depict schematic representations of different embodiments of an augmented and/or virtual reality.

FIG. 2 depicts schematically an exemplary embodiment of the augmented and/or virtual reality, in particular, from a viewpoint of the user U. Therein, a hand of the user U may form the input device or system IM. In addition, the user input may have a trajectory, in particular, between a spatial start point and a spatial end point. The display apparatus D may be configured for associating the spatial start point with a gripping point GP, in particular, on a corner and/or an edge and/or a contour and/or an image point of the planning dataset DS. The display apparatus D may further be configured for generating and displaying the augmented and/or virtual reality based on the planning dataset DS and the projection mappings PI1 and PI2. In particular, the display apparatus D may be configured for generating the augmented and/or virtual reality such that the planning dataset DS is displayed as spaced in relation to a graphical representation of the projection mappings PI1 and PI2. Furthermore, the display apparatus D may be configured for displaying at least one segmented portion of the planning dataset DS, for example, a bone structure and/or a tissue region, in particular, three-dimensionally, for example, as a volumetric mesh model in the augmented and/or virtual reality. Furthermore, the display apparatus D may be configured for generating the augmented and/or virtual reality such that both the planning dataset DS and also the projection mappings PI1 and PI2 are perceivable optically at least partially, in particular, simultaneously, by the user U. Thereby, the planning dataset DS may map the examination region UB pre-procedurally. Furthermore, the image dataset, in particular, the projection mappings PI1 and PI2, may map the examination region UB intra-procedurally, a medical object MD being arranged in the examination region UB. Consequently, the projection mappings PI1 and PI2 may each have a projection mapping of the examination region UB, in particular, intra-procedurally, with the medical object MD arranged therein, along different projection directions PD1 and PD2.

In addition, the planning dataset DS and/or the image dataset may have a predetermined item of image information. Therein, the display apparatus D may be configured for generating and displaying the augmented and/or virtual reality additionally based on the predetermined image information. The predetermined image information may include a preprocessed image information item, (e.g., an image gradient, an edge image, a probability image, or combination thereof), having an item of probability information with regard to the presence of a particular structure. Alternatively or additionally, the predetermined image information may include a two-dimensional segmentation of, in particular anatomical, landmarks and/or structures, for example, a vessel and/or a bone structure and/or an organ and/or a tissue region, and/or a medical object, for example, a catheter and/or a guide wire and/or an endoscope. FIG. 2 depicts schematically a segmented bone structure, in particular, a skull, from the planning dataset DS in the augmented and/or virtual reality, by way of example, for a predetermined item of image information.

The display apparatus D may also be configured for selecting and/or generating the predetermined image information based on the user input.

Advantageously, the image dataset may have metadata, wherein the metadata has an item of information relating to a recording geometry and/or an operating parameter of the medical imaging device for recording the image dataset. Furthermore, the display apparatus D may be configured, based on the metadata, to arrange a virtual source Q1 or Q2, for example, a virtual X-ray source in the augmented and/or virtual reality in relation to the projection mappings PI1 and PI2 according to the respective recording geometry.

In addition, the display apparatus D may be configured for generating and displaying the augmented and/or virtual reality having at least one virtual auxiliary element to the projection mappings PI1 and PI2. The virtual auxiliary element may have a graphical representation, in each case, of a projection cone and/or of a central ray of the virtual sources Q1 and Q2 along the respective, in particular, virtual projection direction PD1 and PD2.

Figure 3:
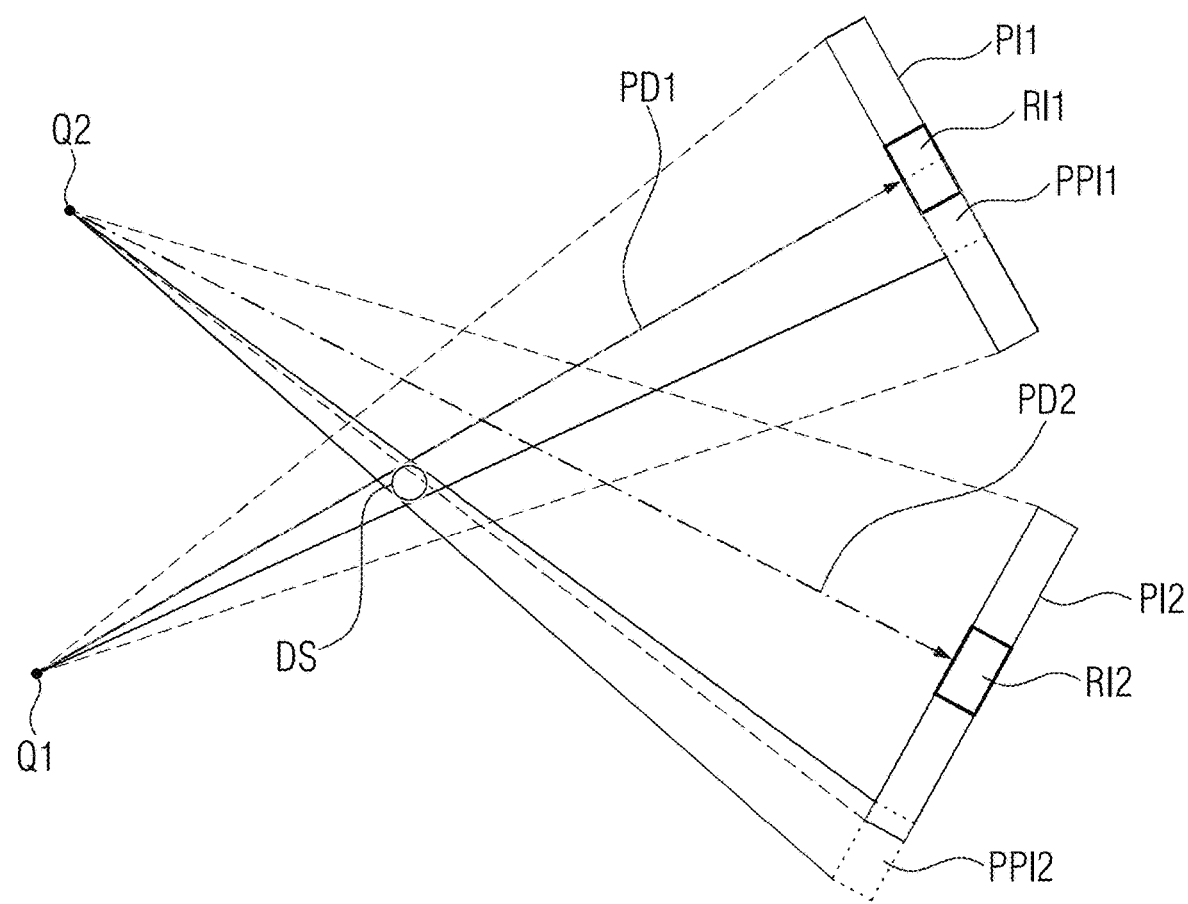
Figure 4:
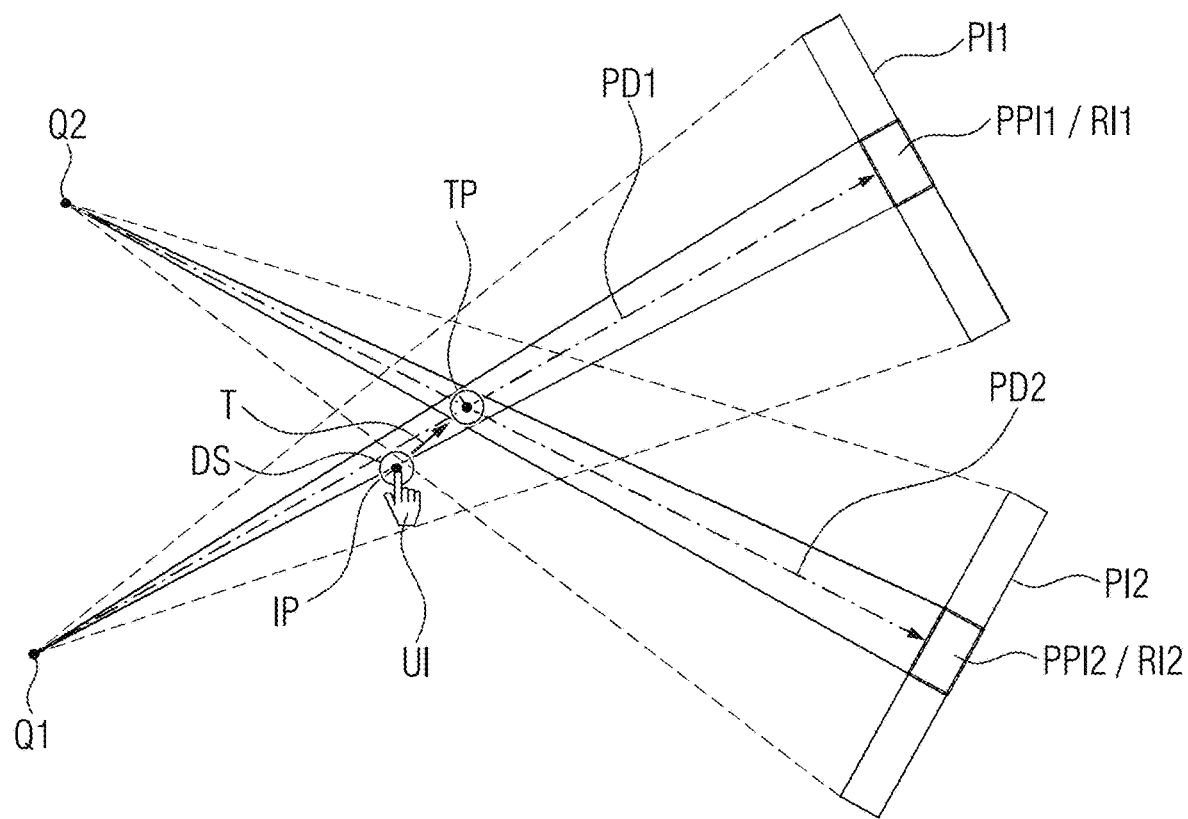

In FIGS. 3 and 4, in each case, an exemplary virtual spatial arrangement of the planning dataset DS and of the projection mappings PI1 and PI2 are shown schematically in the augmented and/or virtual reality. Therein, the display apparatus D may be configured for generating planning projection mappings PPI1 and PPI2 of the planning dataset DS, in particular, along the projection directions PD1 and PD2 of the projection mappings PI1 and PI2. The display apparatus D may further be configured for generating and displaying the augmented and/or virtual reality based on the planning projection mappings PPI1 and PPI2. Furthermore, the display apparatus D may be configured for adapting the planning projection mappings PPI1 and PPI2 on a change of the virtual spatial positioning of the planning dataset DS relative to the projection mappings PI1 and PI2.

In other words, in each case, one of the projection directions PD1 and PD2 of the projection mappings PI1 and PI2 are specified as a virtual projection direction for generating the planning projection mappings PPI1 and PPI2. Thereby, it may be achieved that the mapping geometry for virtual projection mapping of the planning dataset DS along the virtual projection directions starting from the virtual sources Q1 and Q2 advantageously corresponds to the recording geometry for recording the projection mappings PI1 and PI2. Advantageously thereby, an intuitive repositioning of the planning dataset DS relative to the projection mappings PI1 and PI2 in the augmented and/or virtual reality is enabled such that the planning projection mappings PPI1 and PPI2 may be brought into conformity, in each case, with one of the projection mappings PI1 and PI2, in particular, with a reference portion RI1 and RI2 within the projection mappings PI1 and PI2. Thus, the examination region UB of the examination object 31 mapped in the planning dataset DS may be virtually positioned in relation to the virtual sources Q1 and Q2, the virtual projection direction and/or the planning projection mappings PPI1 and PPI2 such that a deviation between the mapping geometry for generating the planning projection mappings PPI1 and PPI2 and the recording geometry for recording the projection mappings PI1 and PI2 is minimized.

Shown schematically in FIG. 4 is an exemplary virtual repositioning of the planning dataset in the augmented and/or virtual reality. The sensor unit S may therein advantageously be configured for capturing an initial spatial positioning of the user input UI, in particular, the input device or system IM at a start point IP, in particular, a start point of the trajectory T. Similarly thereto, the sensor unit may be configured for capturing a final spatial positioning of the user input UI, in particular, the input device or system IM at the end point TP.

The display apparatus D may be configured for determining a transformation rule for adapting the virtual spatial positioning of the planning dataset DS relative to the projection mappings PI1 and PI2, based on the user input UI. Furthermore, the display apparatus may be configured for specifying at least one spatial degree of freedom of the transformation rule based on a geometric property of the planning dataset DS and/or the image dataset.

The display apparatus D may be configured for adapting the virtual spatial positioning of the planning dataset DS, in particular, the gripping point GP, relative to the projection mappings PI1 and PI2 according to the user input UI. The display apparatus D may be configured for repositioning the gripping point GP in the augmented and/or virtual reality from the start point IP to the end point TP. Furthermore, the display apparatus D may be configured for adapting and displaying the augmented and/or virtual reality during and/or after the user input UI.

Figure 5:
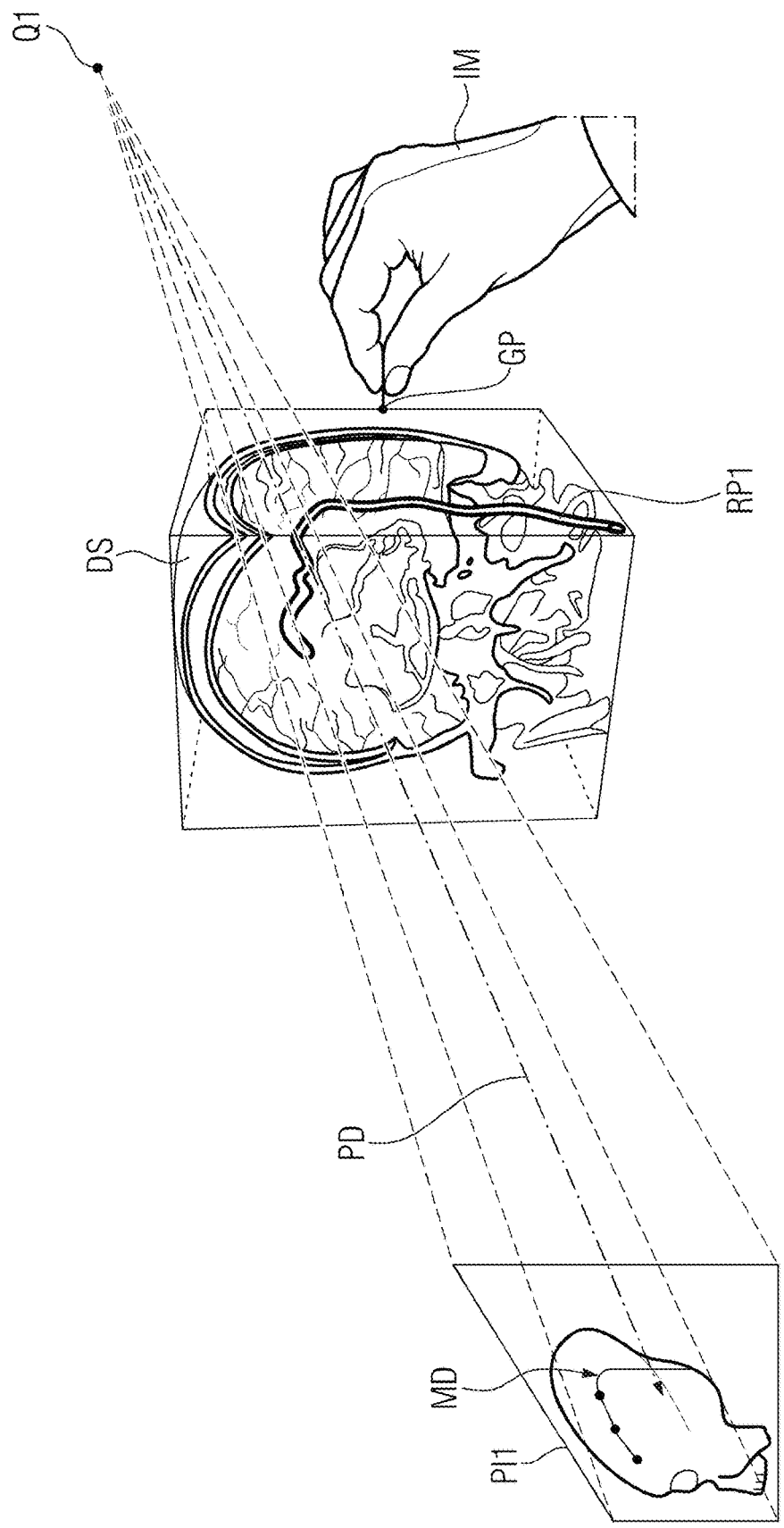

FIG. 5 depicts a further exemplary embodiment of the augmented and/or virtual reality, in particular, from the viewpoint of the user U. Therein, the display apparatus D may be configured for generating a back projection RP1 of the projection mapping PI1. Furthermore, the display apparatus D may be configured for generating and displaying the augmented and/or virtual reality additionally based on the back projection RP1.

The back projection RP1 may include a virtual, in particular, filtered back projection of the projection mapping PI1 onto the planning dataset DS. Therein, the display apparatus D may be configured for generating the back projection RP1 along the projection direction of the respective projection mapping toward the virtual source. The display apparatus D may be configured, in particular, for generating and displaying the back projection RP1 and the planning dataset DS in the augmented and/or virtual reality at least partially transparently and/or, in particular mutually, overlaid. In the exemplary embodiment shown in FIG. 5, for example, the medical object MD mapped in the projection mapping PI1 may be back projected and displayed on a mapping of a vessel structure mapped and/or segmented in the planning dataset DS.

The display apparatus D may further be configured for adapting the back projection RP1 on a change of the virtual spatial positioning of the planning dataset DS relative to the projection mapping PI1.

Figure 6:
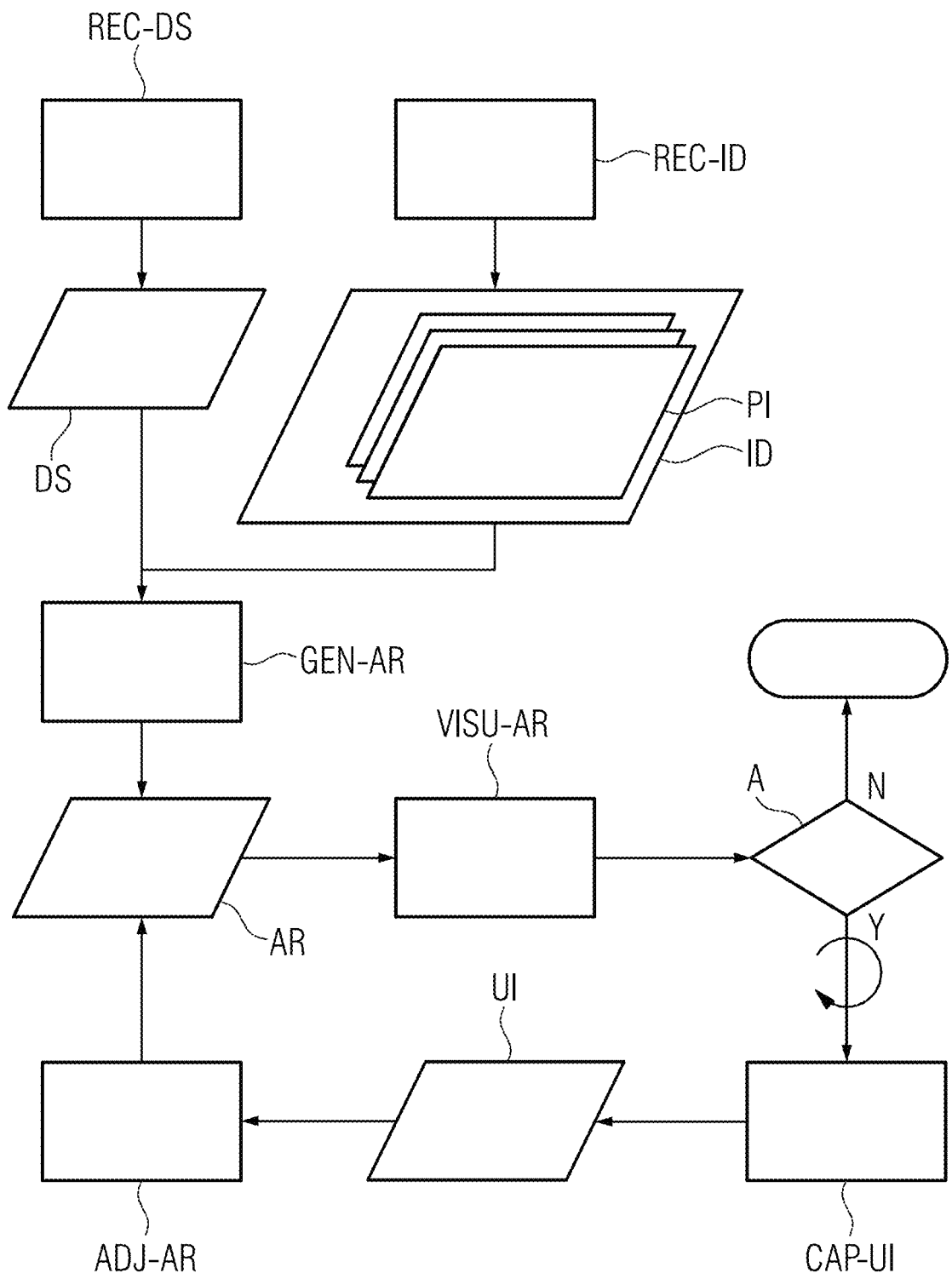
FIGS. 6 to 8 depict schematic representations of different embodiments of a proposed method for registering a planning dataset with an image dataset.

FIG. 6 depicts schematically an advantageous embodiment of a proposed method for registering a planning dataset DS with an image dataset ID. Therein, in act a), the planning dataset DS may be received REC-DS. Furthermore, in act b), the image dataset ID having at least one projection mapping PI may be received REC-ID. Thereafter, the augmented and/or virtual reality AR may be generated GEN-AR based on the planning dataset DS and the at least one projection mapping PI in act c). In act d), a graphical display of the augmented and/or virtual reality AR may be displayed VISU-AR by the display apparatus D, in particular by the first display unit. In act e), a user input UI may be captured CAP-UI by the sensor unit S. Furthermore, in act f), the virtual spatial positioning of the planning dataset DS relative to the at least one projection mapping PI may be adapted ADJ-AR in the augmented and/or virtual reality AR based on the user input UI. Therein, the acts d) to f) may be repeatedly executed until the occurrence of a termination condition A.

Furthermore, act c) may include an application of a transformation rule for registering the planning dataset DS with the image dataset ID.

Figure 7:
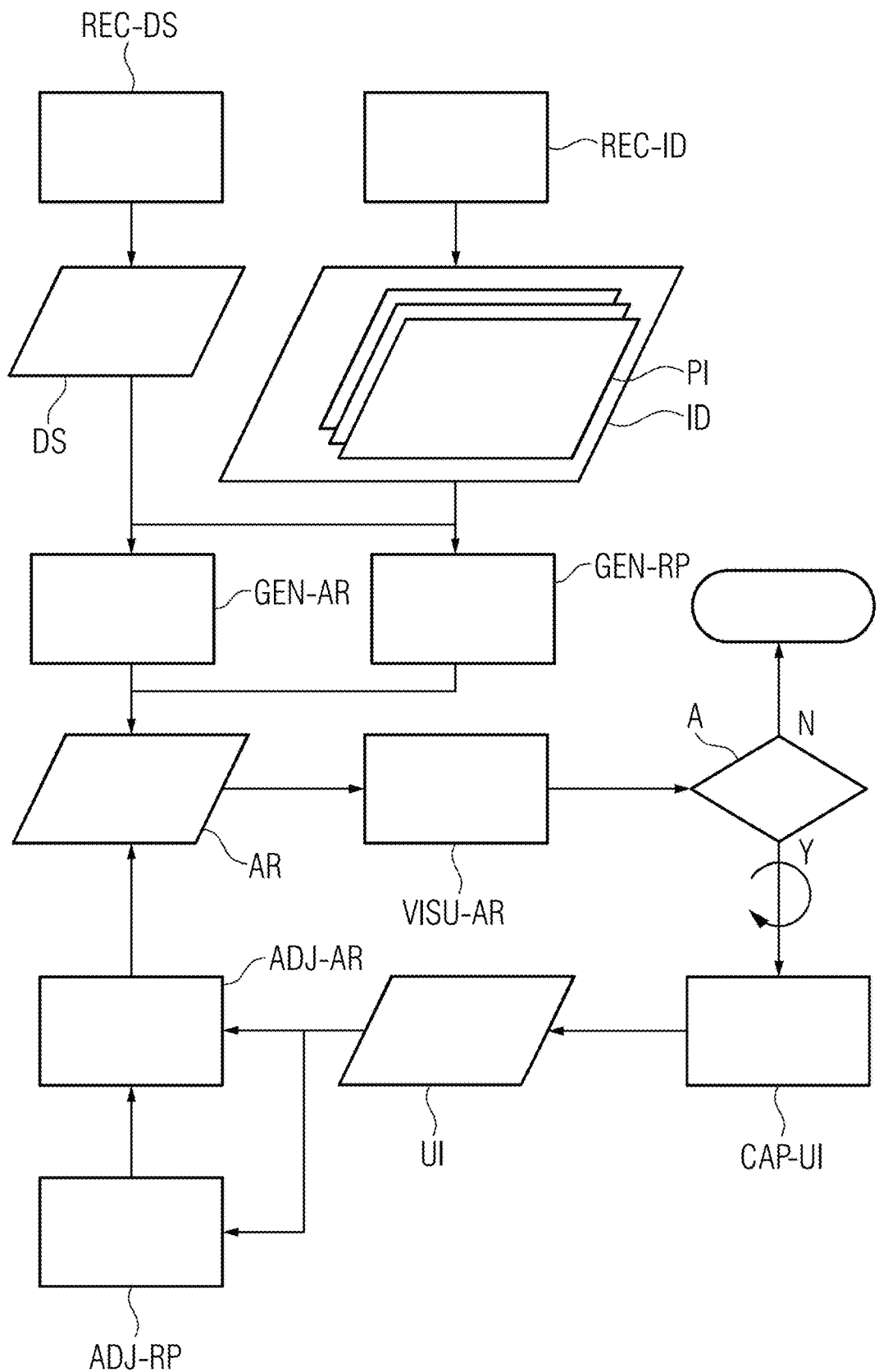

FIG. 7 depicts schematically a further advantageous embodiment of a proposed method for registering a planning dataset DS with an image dataset ID. Therein, act c) may further include a generation GEN-RP of a back projection of the at least one projection mapping PI. Furthermore, the augmented and/or virtual reality AR may additionally be generated based on the at least one back projection. In addition, act f) may include an adaptation ADJ-RP of the at least one back projection on a change of the virtual spatial positioning of the planning dataset DS relative to the at least one projection mapping PI. Advantageously, the termination condition A may include a comparison between a further similarity measure and a specified further threshold value, wherein the further similarity measure evaluates a conformity between the at least one back projection and the planning dataset DS.

Figure 8:
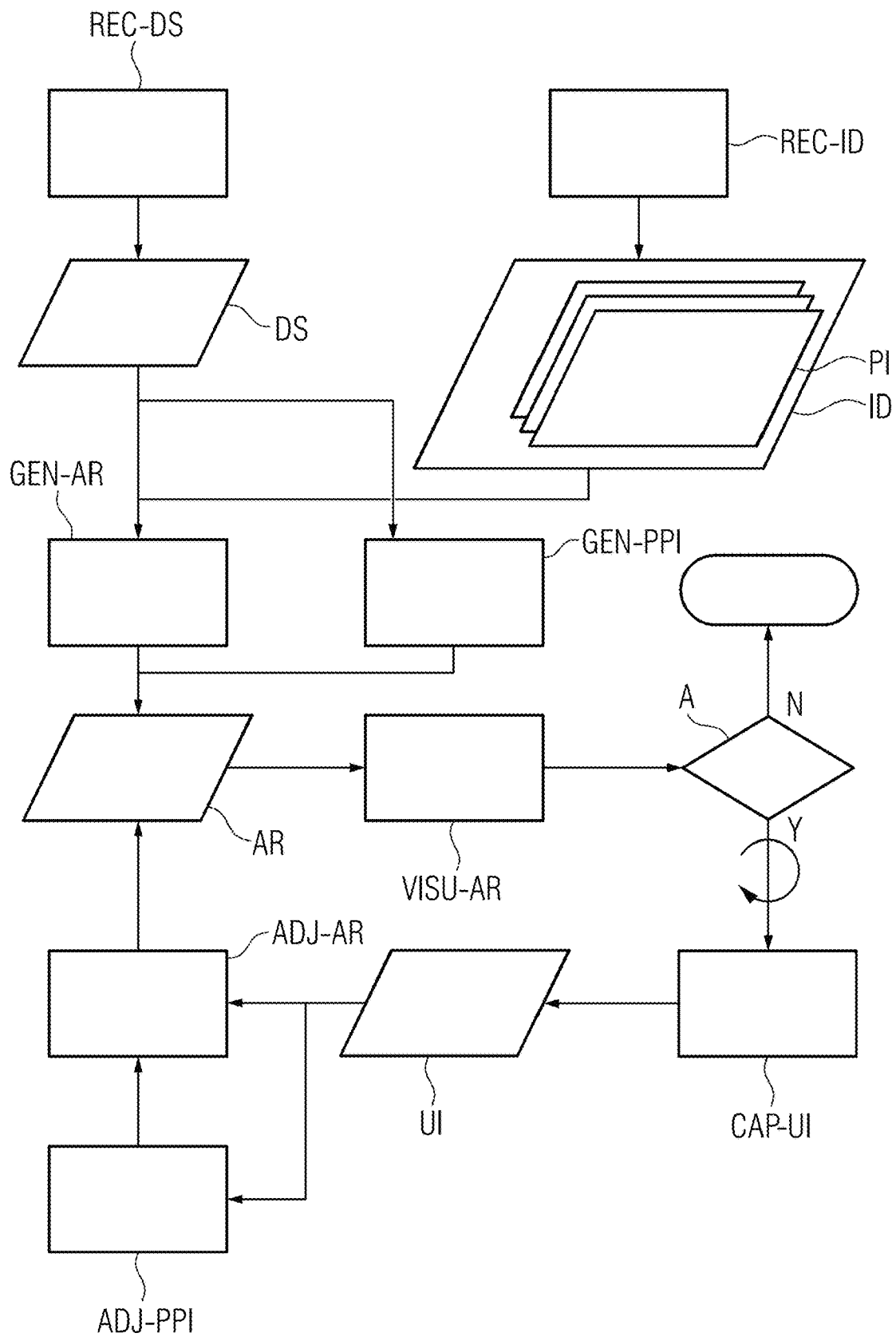

FIG. 8 depicts schematically a further advantageous embodiment of the proposed method for registering a planning dataset DS with an image dataset ID. Therein, act c) may further include a generation GEN-PPI of at least one planning projection mapping. Furthermore, the augmented and/or virtual reality AR may additionally be generated based on the at least one planning projection mapping. In addition, act f) may include an adaptation ADJ-PPI of the at least one planning projection mapping on a change of the virtual spatial positioning of the planning dataset DS relative to the at least one projection mapping PI. Advantageously, the termination condition A may include a comparison between a similarity measure and a specified threshold value, wherein the similarity measure evaluates a conformity between the at least one planning projection mapping and the at least one projection mapping DS.

The schematic representations contained in the figures described do not show any scale or size relation.

Further, the methods described above in detail and the apparatuses disclosed are merely exemplary embodiments which may be modified by a person skilled in the art in a wide variety of ways without departing from the scope of the disclosure. Furthermore, the use of the indefinite article "a" or "an" does not preclude the possibility that the relevant features may also be present plurally. Similarly, the expressions "unit" and "element" do not preclude the components in question including a plurality of cooperating subcomponents with may also be spatially distributed, where relevant.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described more specifically in detail by the exemplary embodiments, the disclosure is not restricted by the disclosed examples and other variations may be derived therefrom by a person skilled in the art without departing from the scope of protection of the disclosure.

The invention claimed is:

1. A display apparatus for displaying an augmented and/or virtual reality, the display apparatus comprising:
a sensor unit configured to capture a user input, wherein the sensor unit is further configured to capture an initial spatial positioning and a final spatial positioning based on the user input, and wherein the user input comprises a trajectory between the initial spatial positioning and the final spatial positioning,
wherein the display apparatus is configured to:
receive a medical image dataset of an examination object, the medical image dataset comprising at least one projection mapping;
receive a medical planning dataset of the examination object;
generate and display the augmented and/or virtual reality based on the at least one projection mapping and the medical planning dataset;
determine a transformation rule for adapting a virtual spatial positioning of the medical planning dataset relative to the at least one projection mapping based on a captured change between the initial spatial positioning and the final spatial positioning along the trajectory of the user input; and
adapt the virtual spatial positioning of the medical planning dataset relative to the at least one projection mapping in the augmented and/or virtual reality based on the user input such that a gripping point is repositioned from the initial spatial positioning to the final spatial positioning when the transformation rule is applied.

2. The display apparatus of claim 1, wherein the display apparatus is further configured to:
generate at least one planning projection mapping of the medical planning dataset,
generate and display the augmented and/or virtual reality additionally based on the at least one planning projection mapping, and
adapt the at least one planning projection mapping on a change of the virtual spatial positioning of the medical planning dataset relative to the at least one projection mapping.

3. The display apparatus of claim 2, further comprising:
a first display unit configured to display the augmented and/or virtual reality; and
a second display unit configured to display the at least one projection mapping and/or the at least one planning projection mapping,
wherein the sensor unit is further configured to capture a spatial relative positioning of the first display unit and the second display unit relative to one another, and
wherein the display apparatus is further configured to adapt the augmented and/or virtual reality based on of the captured relative positioning.

4. The display apparatus of claim 2, wherein the display apparatus is further configured to generate the at least one planning projection mapping along a projection direction of the at least one projection mapping.

5. The display apparatus of claim 1, wherein the display apparatus is further configured to:
generate at least one back projection of the at least one projection mapping,
generate and display the augmented and/or virtual reality additionally based on the at least one back projection, and
adapt the at least one back projection on a change of the virtual spatial positioning of the medical planning dataset relative to the at least one projection mapping.

6. The display apparatus of claim 1, wherein the display apparatus is further configured to specify at least one spatial degree of freedom of the transformation rule based on a geometric property of the medical planning dataset and/or the medical image dataset.

7. The display apparatus of claim 1, wherein the sensor unit comprises an optical sensor, a haptic sensor, an electromagnetic sensor, an acoustic sensor, an eye tracker, or a combination thereof, and
wherein the sensor unit is configured to capture the user input, a positioning of at least one body part of a user, a movement of the at least one body part of the user, a speech input by the user, a gaze direction of the user, or a combination thereof.

8. The display apparatus of claim 1, wherein the medical planning dataset and/or the medical image dataset have a predetermined item of image information, and
wherein the display apparatus is further configured to generate and display the augmented and/or virtual reality additionally based on the predetermined item of image information.

9. The display apparatus of claim 8, wherein the display apparatus is further configured to select and/or generate the predetermined item of image information based on the user input.

10. A system comprising:
a medical imaging device; and
a display apparatus having a sensor unit configured to capture a user input, wherein the sensor unit is further configured to capture an initial spatial positioning and a final spatial positioning based on the user input, and wherein the user input comprises a trajectory between the initial spatial positioning and the final spatial positioning,
wherein the display apparatus is configured to:
receive a medical image dataset of an examination object having at least one projection mapping,
receive a medical planning dataset of the examination object,
generate and display an augmented and/or virtual reality based on the at least one projection mapping and the medical planning dataset,
determine a transformation rule for adapting a virtual spatial positioning of the medical planning dataset relative to the at least one projection mapping based on a captured change between the initial spatial positioning and the final spatial positioning along the trajectory of the user input, and
adapt the virtual spatial positioning of the medical planning dataset relative to the at least one projection mapping in the augmented and/or virtual reality based on the user input such that a gripping point is repositioned from the initial spatial positioning to the final spatial positioning when the transformation rule is applied, and
wherein the medical imaging device is configured to record the medical planning dataset and/or the medical image dataset, receive the medical planning dataset and/or the medical image dataset, provide the medical planning dataset and/or the medical image dataset, or a combination thereof.

11. A method for registering a planning dataset with an image dataset, the method comprising:
receiving the planning dataset of an examination object;
receiving the image dataset of the examination object, the image dataset having at least one projection mapping;
generating an augmented and/or virtual reality based on the planning dataset and the at least one projection mapping of the image dataset;
displaying a graphical display of the augmented and/or virtual reality by a display apparatus having a sensor unit;
capturing a user input by the sensor unit of the display apparatus, wherein the sensor unit further captures an initial spatial positioning and a final spatial positioning based on the user input, and wherein the user input comprises a trajectory between the initial spatial positioning and the final spatial positioning;
determining a transformation rule for adapting a virtual spatial positioning of the planning dataset relative to the at least one projection mapping based on a captured change between the initial spatial positioning and the final spatial positioning along the trajectory of the user input; and
adapting the virtual spatial positioning of the planning dataset relative to the at least one projection mapping in the augmented and/or virtual reality based on the user input such that a gripping point is repositioned from the initial spatial positioning to the final spatial positioning when the transformation rule is applied.

12. The method of claim 11, further comprising:
repeating the displaying, the capturing, and the adapting until an occurrence of a termination condition.

13. The method of claim 12, wherein the generating of the augmented and/or virtual reality further comprises an application of the transformation rule for registering the planning dataset with the image dataset.

14. The method of claim 12, wherein the generating of the augmented and/or virtual reality further comprises a generation of at least one planning projection mapping of the planning dataset along a projection direction of the at least one projection mapping,
wherein the augmented and/or virtual reality is generated additionally based on the at least one planning projection mapping, and wherein the adapting of the virtual spatial positioning further comprises an adaptation of the at least one planning projection mapping on a change of the virtual spatial positioning of the planning dataset relative to the at least one projection mapping.

15. The method of claim 14, wherein the termination condition comprises a comparison between a similarity measure and a specified threshold value, and
wherein the similarity measure evaluates a conformity between the at least one planning projection mapping and evaluates the at least one projection mapping.

16. The method of claim 12, wherein the generating of the augmented and/or virtual reality further comprises a generation of at least one back projection of the at least one projection mapping,
wherein the augmented and/or virtual reality is generated additionally based on the at least one back projection, and
wherein the adapting of the virtual spatial positioning further comprises an adaptation of the at least one back projection mapping on a change of the virtual spatial positioning of the planning dataset relative to the at least one projection mapping.

17. The method of claim 16, wherein the termination condition comprises a comparison between a further similarity measure and a specified further threshold value, and
wherein the further similarity measure is provided to evaluate a conformity between the at least one back projection and the planning dataset.

* * * * *